US00PP17352P2

(12) United States Plant Patent van Manen

(10) Patent No.: US PP17,352 P2

(45) Date of Patent: Jan. 9, 2007

(54) *LONICERA* PLANT NAMED 'MASKERADE'

(50) Latin Name: *Lonicera japonica*
Varietal Denomination: Maskerade

(75) Inventor: Pieter van Manen, Ederveen (NL)

(73) Assignee: Witteman & Co., Hillegom (NL)

( * ) Notice: Subject to any disclaimer, the term of this patent is extended or adjusted under 35 U.S.C. 154(b) by 134 days.

(21) Appl. No.: 11/045,985

(22) Filed: Jan. 28, 2005

(51) Int. Cl.
*A01H 5/00* (2006.01)

(52) U.S. Cl. ..... Plt./226

(58) Field of Classification Search ..... Plt./226, Plt./263

See application file for complete search history.

*Primary Examiner*—Kent Bell

(74) *Attorney, Agent, or Firm*—C. A. Whealy

(57) ABSTRACT

A new and distinct cultivar of *Lonicera* plant named 'Maskerade', characterized by its upright vining plant habit; green and yellow green variegated leaves; and good garden performance.

2 Drawing Sheets

Botanical designation: *Lonicera japonica.*
Cultivar denomination: 'Maskerade'.

BACKGROUND OF THE INVENTION

The present Invention relates to a new and distinct cultivar of *Lonicera* plant, botanically known as *Lonicera japonica*, and hereinafter referred to by the name 'Maskerade'.

The new cultivar is a naturally-occurring branch mutation of an unnamed selection of *Lonicera japonica*, not patented. The new *Lonicera* was discovered and selected as a branch mutation on a single plant of the parent selection by the Inventor in 1995 in a controlled environment in Ederveen, The Netherlands.

Asexual reproduction of the new *Lonicera* by cuttings since 2001 in Ederveen, The Netherlands, has shown that the unique features of this new *Lonicera* are stable and reproduced true to type in successive generations of asexual reproduction.

SUMMARY OF THE INVENTION

The following traits have been repeatedly observed and are determined to be the unique characteristics of 'Maskerade'. These characteristics in combination distinguish 'Maskerade' as a new and distinct cultivar:

1. Upright vining plant habit.
2. Green and yellow green variegated leaves.
3. Good garden performance.

Plants of the new *Lonicera* can be compared to plants of the parent selection and other *Lonicera* selections known to the Inventor. Plants of the new *Lonicera* differ primarily from plants of the parent selection and other *Lonicera* selections known to the Inventor in leaf coloration as plants of the parent selection and other *Lonicera* selections known to the Inventor have non-variegated leaves.

BRIEF DESCRIPTION OF THE PHOTOGRAPHS

The accompanying colored photographs illustrate the overall appearance of the new *Lonicera*, showing the colors as true as it is reasonably possible to obtain in colored reproductions of this type. Colors in the photographs may differ slightly from the color values cited in the detailed botanical description which accurately describe the colors of the new *Lonicera.*

The photograph on the first sheet comprises a side perspective view of a typical plant of 'Maskerade' grown in an outdoor nursery.

The photograph at the top of the second sheet is a close-up view of a typical plant of 'Maskerade'.

The photograph at the bottom of the second sheet is a close-up view of typical leaves of 'Maskerade'.

DETAILED BOTANICAL DESCRIPTION

The new *Lonicera* has not been observed under all possible environmental conditions. The phenotype may vary somewhat with variations in environment such as temperature and light intensity, without, however, any variance in genotype.

The aforementioned photographs, following observations and measurements describe plants grown in Boskoop, The Netherlands, in an outdoor nursery and under commercial production practices. Plants used for the photographs and the description were about two years old. The photographs and description were taken during the early fall with day temperatures ranging from 14 to 27° C. and night temperatures ranging from 7 to 15° C. In the following description, color references are made to The Royal Horticultural Society Colour Chart, 2001 Edition, except where general terms of ordinary dictionary significance are used.

Botanical classification: *Lonicera japonica* cultivar Maskerade.

Parentage: Naturally-occurring branch mutation of an unnamed selection of *Lonicera japonica*, not patented.

Propagation:

*Type.*—By softwood cuttings.

*Time to initiate roots.*—About three weeks at 20° C.

*Time to produce a rooted young plant.*—About two months at 15° C.

*Root description.*—Medium thickness; creamy white in color.

*Rooting habit.*—Moderate branching; moderately dense.

Plant description:

*Plant form.*—Perennial twining vine; mostly upright.

*Growth habit.*—Vigorous; young plants grow about one meter per year. Freely branching; about six lateral branches per plant.

*Plant height* (*length*).—About 170 cm.

*Plant width* (*spread*).—About 26 cm.

*Lateral branch description.*—Length: About 1 meter. Diameter: About 2 mm. Internode length: About 3.2 cm. Strength: Strong. Texture: Sparsely pubescent. Color: Between N172A and 175B to 175C.

*Leaf description.*—Arrangement: Opposite; simple. Length: About 5.5 cm. Width: About 2.5 cm. Shape: Narrowly ovate to elliptic. Apex: Acute. Base: Attenuate. Margin: Mostly entire, but frequently irregular and undulate. Texture, upper and lower surfaces: Pubescence on primary veins and at margins; leathery.

*Color.*—Developing leaves, upper surface: Centers, between 137A and 146A; towards the margins, irregular sectors of 150D to 154C to 154D. Developing leaves, lower surface: Centers, 138B; towards the margins, irregular sectors of 145B to 154D. Fully expanded leaves, upper surface: Centers, 137A; towards the margins, irregular sectors of 150C; venation, 144B. Fully expanded leaves, lower surface: Centers, 138B to 138C; towards the margins, irregular sectors of 145C; venation, 144C.

*Petiole length.*—About 6 mm.

*Petiole diameter.*—About 1 mm.

*Petiole texture, upper and lower surfaces.*—Sparsely pubescent.

*Petiole color.*—176B to 143B.

Flower description: Flower development has not been observed on plants of the new *Lonicera.*

Disease/pest resistance: Plants of the new *Lonicera* have not been observed to be resistant pathogens or pests common to *Lonicera.*

Garden performance: Plants of the new *Lonicera* have been observed to have good garden performance and tolerate rain wind and temperatures ranging from −5 to 35° C.

It is claimed:

1. A new and distinct cultivar of *Lonicera* plant named 'Maskerade', as illustrated and described.

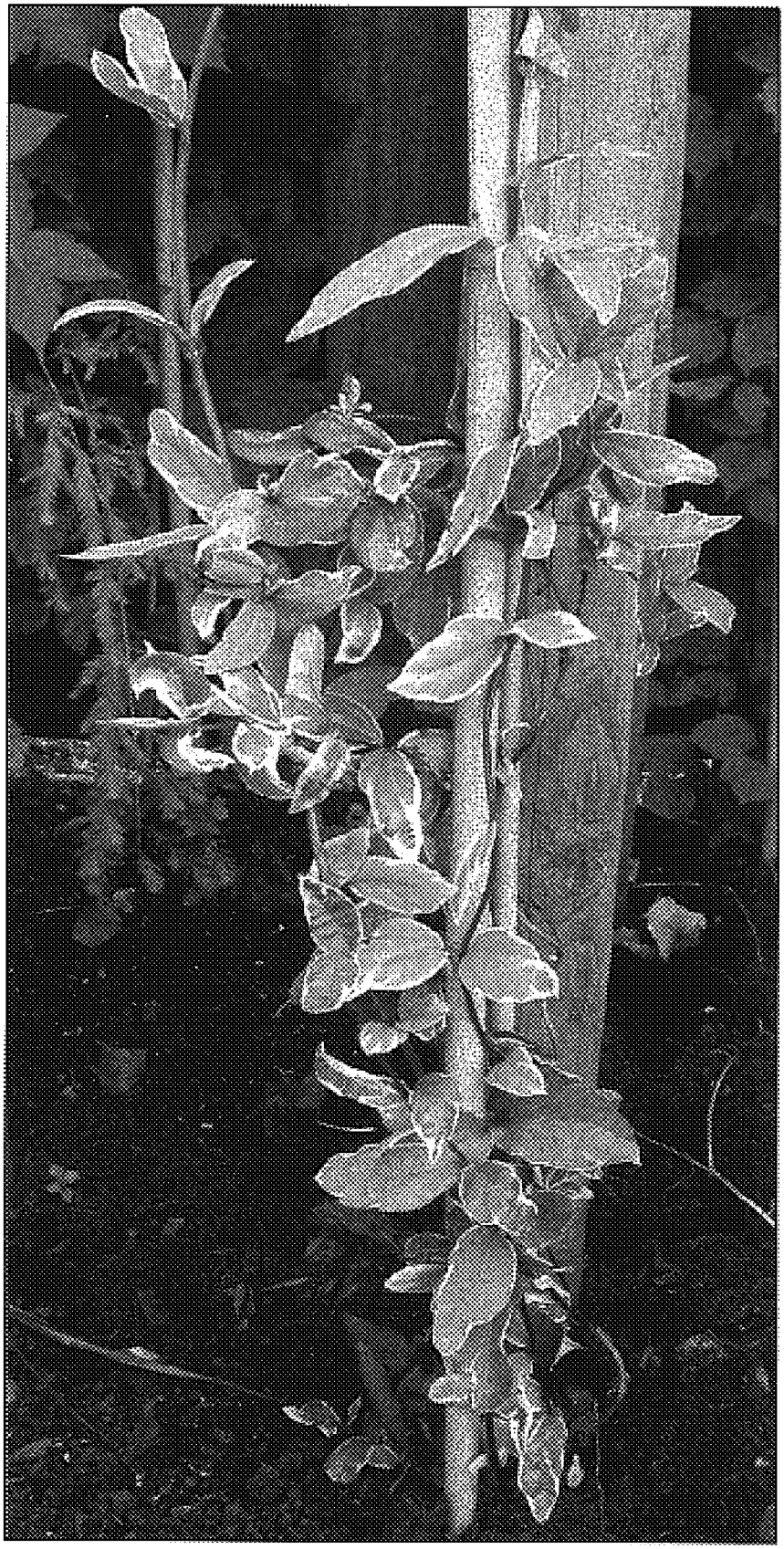

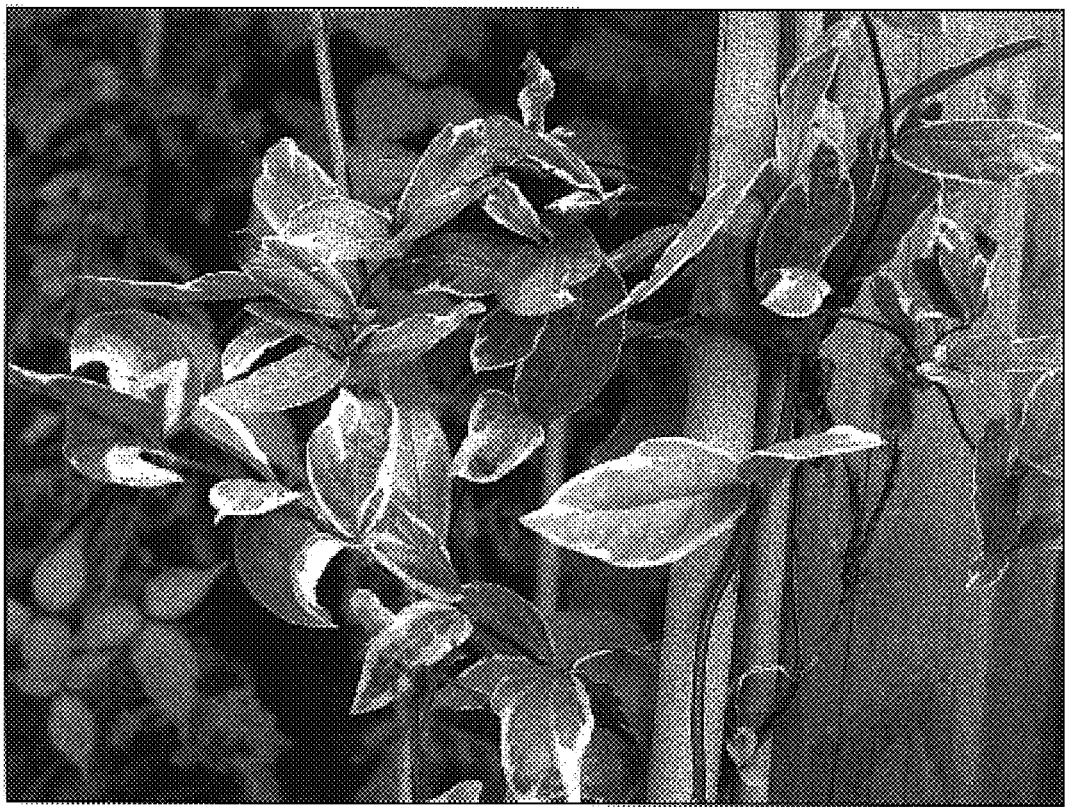
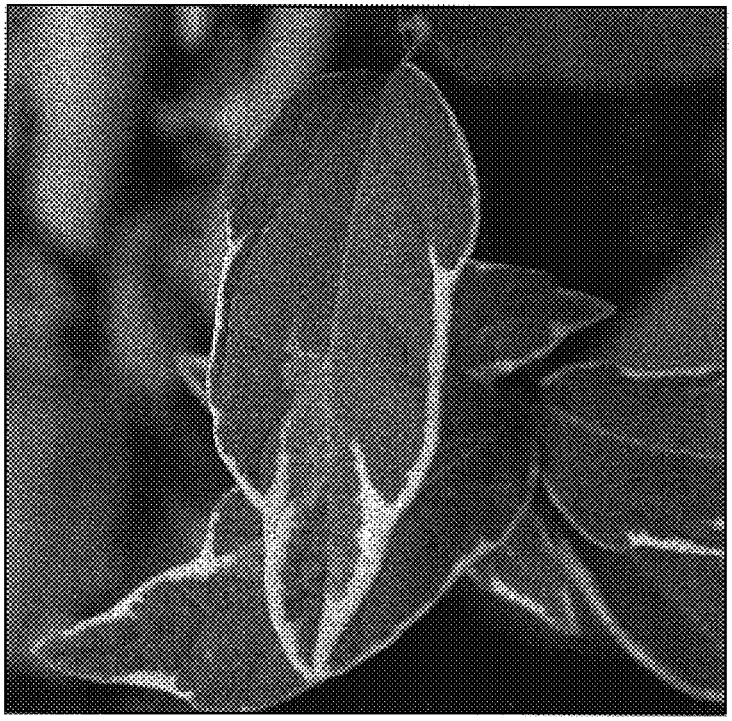

* * * * *